(12) United States Patent
Son et al.

(10) Patent No.: US 8,575,089 B2
(45) Date of Patent: Nov. 5, 2013

(54) COMPOSITION FOR PREVENTING OR TREATING INFLAMMATION

(75) Inventors: Young Sook Son, Seoul (KR); Hyun Sook Hong, Seoul (KR); Do Yeon Kim, Gwangmyeong-si (KR); Eun Kyung Lee, Suwon-si (KW)

(73) Assignee: University-Industry Cooperation Group of Kyung Hee, Yongin-si (KR)

( * ) Notice: Subject to any disclaimer, the term of this patent is extended or adjusted under 35 U.S.C. 154(b) by 0 days.

(21) Appl. No.: 13/390,888

(22) PCT Filed: Aug. 17, 2010

(86) PCT No.: PCT/KR2010/005420
§ 371 (c)(1),
(2), (4) Date: Feb. 16, 2012

(87) PCT Pub. No.: WO2011/021833
PCT Pub. Date: Feb. 24, 2011

(65) Prior Publication Data
US 2012/0214729 A1    Aug. 23, 2012

(30) Foreign Application Priority Data
Aug. 17, 2009    (KR) .................. 10-2009-0075881

(51) Int. Cl.
*A61K 38/00*    (2006.01)
*A61P 5/00*    (2006.01)
(52) U.S. Cl.
USPC ........... 514/1.4; 514/886; 514/18.6; 514/18.7
(58) Field of Classification Search
None
See application file for complete search history.

(56) References Cited

U.S. PATENT DOCUMENTS

2005/0075701 A1    4/2005    Shafer

FOREIGN PATENT DOCUMENTS

EP    1 308 165 A1    5/2003
WO    2009/017655 A2    2/2009

OTHER PUBLICATIONS

O'Connor et al "The Role of Substance P in Inflammatory Disease" J Cellular Phys 201:167-180. Published Mar. 19, 2004.*
McClellan et al "Substance P Promotes Susceptibility to *Psuedomonas aeruginosa* Keratitis in Resistant Mice:Anti-inflammatory Mediators Downregulated" Investigative Ophthalmology and Visual Science 49:1502-1511. Published Apr. 2008.*
Bremer and Leeman "Substance P" Encyclopedia of Life Sciences. Published 2010.*
Tsui et al., "'Sensing' autoimmunity in type 1 diabetes," *TRENDS in Molecular Medicine 13*(10):405-413, 2007.
Huston et al., "Sequence-specific effects of neurokinin substance P on memory, reinforcement, and brain dopamine activity," *Psychopharmacology 112*:147-162, 1993.

* cited by examiner

*Primary Examiner* — Cecilia J Tsang
*Assistant Examiner* — Zachary J Miknis
(74) *Attorney, Agent, or Firm* — Seed IP Law Group PLLC

(57) ABSTRACT

The present invention relates to a composition containing Substance P for preventing or treating an inflammation. The composition containing Substance P according to the present invention exhibits the effect of decreasing leukocytes, neutrophils and hematopoietic stem cells in a blood, which are associated with the inflammation, and of increasing anti-inflammatory cytokines, regulatory T-lymphocytes, anti-inflammatory macrophages and the like, thereby terminating inflammatory response at an early stage, and is thus highly effective in preventing and treating the inflammation caused by a non-traumatic, traumatic, infectious or ischemic retinal injury.

10 Claims, 7 Drawing Sheets

PB: Peripheral Blood (A) Co-injection of SP and STZ (B) SP Injection after inducing diabetes by STZ (C) Diabetes induction by STZ

COMPOSITION FOR PREVENTING OR TREATING INFLAMMATION

CROSS REFERENCE TO RELATED APPLICATIONS

This application is a United States national stage application filed under 35 U.S.C. §371 of International Application No. PCT/KR2010/005420, accorded an international filing date of Aug. 17, 2010; which application claims priority to Korean (KR) Patent Application No. 10-2009-0075881, filed Aug. 17, 2009; all of which applications are incorporated herein by reference in their entirety.

TECHNICAL FIELD

The present invention relates to a composition for preventing and treating an inflammation, in which the composition includes Substance-P as an active ingredient.

BACKGROUND ART

Inflammation is induced in many conditions, including various tissue injuries and necrosis (a traumatic injury, a radiation injury, a cell injury due to an anti-cancer drug, an ischemic injury, a non-traumatic autoimmune disease, a tissue injury due to a rejection of transplant, and the like), foreign substance reaction, and infection. Inflammation may be locally induced or may be developed in response to sepsis, which induces inflammation all over the body, according to the degree of severity. Inflammation is a main cause of diseases for a large number of inflammatory diseases, for example, sepsis, arthritis, asthma, respiratory disease, respiratory syncitial virus (RSV) disease, radiation injury, stomach ulcer, gastroenteritis, diabetic ulcer, bedsore, nerve spinal injury, dementia, cornea injury, a skin wound, atopic dermatitis, cardiovascular disorders, autoimmune disease, rejection reaction of transplant, and the like, so that recently, many researchers are trying to inhibit inflammation processes. Continuous inflammation accelerates damage of tissue, so that nothing is more important than suitable inhibition of inflammation for treatment and survival of a patient.

An inflammatory cell is generated through several steps of differentiation processes from hematopoietic stem cells (HSC) in bone marrow like other hemocytes, and it is a one-way reaction so that once the cell is differentiated, the cell cannot be again returned to an undifferentiated state. Accordingly, as in the case of the other hemocytes, its life span is limited to between several days and several weeks, except for lymphocytes. Therefore, the generation of the cells of hematopoietic system occurs by continuous cell divisions and differentiations from hematopoietic stem cells throughout life. When an increase in inflammatory cells is required due to a tissue injury, the amount of HSC precursor cells having rapid division ability in bone marrow is increased so that the amount of hematopoietic stem cells is also increased in blood. The increased HSC begins to differentiate to a type of commitment hematopoietic progenitor cell. Therefore, a change of the amount of HSC in blood may significantly affect overall inflammation and immune response.

Inflammation is characterized by increased distributions of inflammatory hemocytoblasts (leukocytes, neutrophils, macrophages, and the like), precursor cells thereof, and HSCs in blood, an increase of inflammatory cytokines (TNF-alpha, IL2, IL4, IL6, and the like), and a decrease of anti-inflammatory cytokine (IL10, and the like) (Eva Mezey et al., Nature Medicine 2009, 15, 42-49). In addition, many inflammatory cells accumulate at a damaged tissue.

Generally, inflammation is one of the vital defense mechanisms in innate immune responses, but reactive oxygens, proteases, and the like that are secreted by inflammatory cells, especially, neutrophils, lead to severe injury of the surrounding tissues. Accordingly, an inflammation reaction is prolonged, thereby developing into a chronic or intractable ulcer, etc., which fibroses after curing, thereby causing sclerosis of tissue and so significantly decreasing tissue function.

A drug, such as an adrenocortical hormone and an anti-inflammatory analgesic drug, is now in use in order to treat inflammation, but an increased understanding at a molecular level about inflammation is expected to lead to development of a new drug for treating inflammation.

Recently, it is expected that IL-10, an anti-inflammatory cytokine, which is known to be secreted from anti-inflammatory macrophages (M2 type macrophage), regulatory T cells involved in inhibiting an autoimmune response, and the like, is involved in a decrease of inflammation and a decrease of autoimmune response, thereby minimizing tissue injury due to the inflammation and accelerating cure of tissue injury. There were attempts to control inflammation and autoimmune diseases by accelerating and controlling in vivo anti-inflammatory reaction based on the above-mentioned recent research results. However, a new material having a function for controlling inflammation has yet to be found.

Substance-P (hereinafter referred to as 'Substance P' or 'SP') has long been known to be a neurotransmitter transmitting pain in the central nervous system for. Substance-P is a peptide, which is composed of 11 amino acids, and a kind of neurohormone, in which there is no difference among species because it has the same amino acid sequence in human, mouse, and rabbit. Substance-P is expected to play an important role in a neuro-immune systems bidirectional regulation, myelofibrosis, cancer cell proliferation, and the like, in addition to pain transmission that is conventionally known, through expression and action in various tissues, such as non-nervous tissues, and the like, as well as nerve cells. In addition, the previous reports about Substance-P disclosed that Substance-P accelerates histamine release in a mast cell (Castellani M L et al., Clin Invest. Med. 2008, 31, E362-72), induces allodynia (McLeod A L et al., Neuroscience, 1999, 89, 891-9), and involves peripheral neuritis (Black P H, Brain Behay. Immun. 2002, 16, 622-53). It could be expected based on the above-mentioned reports that Substance-P may be a neurohormone inducing inflammation (proinflammatory neuropeptide) and may induce the same or more inflammation than that of G-CSF.

However, while comparing a function of Substance-P with a function of G-CSF, the present inventors found that Substance-P has rather an effect of inhibiting inflammation in various tissue injuries and thus completed the present invention.

DISCLOSURE

Technical Problem

The present inventors provide a composition for preventing or treating inflammation, in which the composition includes Substance-P as an active ingredient.

Technical Solution

The present invention provides a composition for preventing and treating inflammation, in which the composition includes Substance-P as an active ingredient.

Also, the present invention provides a composition for preventing or treating various inflammations by decreasing inflammatory cells (such as, leukocyte, neutrophils, macrophage, and the like), a hematopoietic stem cell, a mononuclear cell, or inflammatory cytokines (such as, TNF-alpha, IL2, IL4, IL6, and the like), in blood, or increasing anti-inflammatory cytokines (such as IL10, and the like) and anti-inflammatory cells (such as, anti-inflammatory regulatory T cells, anti-inflammatory macrophages (M2), and the like), in blood, in which the composition includes Substance-P as an active ingredient.

In addition, the present invention provides a composition for preventing or treating inflammatory diseases or disorders selected from the group consisting of sepsis, arthritis, asthma, respiratory disease, respiratory syncitial virus (RSV) disease, inflammation induced by radiation, radiation injury, stomach ulcer, gastroenteritis, diabetic ulcer, bedsore, nerve spinal injury, dementia, cornea injury, skin wound, atopic dermatitis, cardiovascular disorders, autoimmune diseases, and rejection reaction of transplant.

The autoimmune disease includes rheumatoid arthritis, progressive systemic sclerosis, systemic lupus erythematous, Type I Diabetes or insulin-dependent diabetes, atopic dermatitis, alopecia greata, psoriasis, Pemphigus, aphthous stomatitis, chronic thyroiditis, some acquired aplastic anemia, primary cirrhosis (primary biliary cirrhosis), Behcet's disease, Crohn's disease, silicosis, asbestos, IgA renal disease, Post-streptococcal acute glomerulonephritis (PSGN), Sjogren's syndrome, Guilian-Barre syndrome, dermatomyositis, polymyositis, multiple sclerosis, autoimmune hemolytic anemia, autoimmune encephalomyelitis, myasthenia gravis, Grave's disease, polyarteritis nodosa, ankylosing spondylitis, fibromyalgia syndrome, and temporal arteritis. Hereinafter, the autoimmune diseases for the present invention refer to as mentioned above.

Also, the present invention provides a composition for preventing or treating inflammatory diseases or disorders selected from the group consisting of sepsis, arthritis, asthma, respiratory disease, respiratory syncitial virus (RSV) infection, gastritis, enteritis, gastroenteritis, and atopic dermatitis.

In addition, the present invention provides a composition for preventing or treating inflammation, which is mediated by at least one or mediates at least one selected from the group consisting of respiratory disease, radiation injury, stomach ulcer, diabetic ulcer, bedsore, nerve spinal injury, dementia, cornea injury, skin wound, cardiovascular disorders, autoimmune disease, and rejection reaction of transplant.

The composition comprising Substance-P as an active ingredient according to the present invention may be prepared by using pharmaceutically suitable and physiologically acceptable additives in addition to the active ingredient, and the additives may include excipients, disintegrant, a sweetener, a binding agent, a coating agent, an expansion agent, a lubricant, a glidant, a flavoring agent, and the like.

The composition comprising Substance-P as an active ingredient according to the present invention may be preferably formulated as a pharmaceutical composition by further including at least one of pharmaceutical acceptable carriers in addition to the above-mentioned active ingredient for administrating.

A pharmaceutical formulation of the composition comprising Substance-P as an active ingredient may be granules, powders, tablets, coated tablets, capsules, syrup, juice, a suspension, an emulsion, an ointment, cream, gel, medicinal drops, aerosol, an injectable liquid formulation, and the like.

For example, an active ingredient may be combined with oral and non-toxic, pharmaceutically acceptable inert carriers, such as ethanol, glycerol, water, and the like, in order to formulate as a type of tablets or capsules. In addition, if it is necessary or required, suitable binding agents, lubricants, disintegrants and coloring agents may be also included in a mixture. The suitable binding agent includes natural sugars, such as starch, gelatin, glucose, or beta-lactose, corn sweetening agents, natural or synthetic gums, such as acacia, tragacanth, or sodium oleate, sodium stearate, magnecium stearate, sodium benzoate, sodium acetate, sodium chloride, and the like, but is not limited thereto. The disintegrant includes starch, methylcellulose, agar, bentonite, xanthan gum, and the like, but is not limited thereto.

Pharmaceutically acceptable carriers for a composition formulated with a liquid solution may be suitable for a sterilization and for administration to a body, and may be saline solution, sterilized water, Ringer solution, buffered saline solution, albumin injection solution, dextrose solution, malto dextrin solution, glycerol, ethanol, and the mixture of at least one thereof, and other general additives, such as antioxidants, a buffering solution, bacteristat, and the like may be added as needed. In addition, tablets, granules, capsules, a pill, a dosage form for injecting, such as an aqueous solution, a suspension, an emulsion, and the like may be formulated by additionally adding a diluent, a dispersing agent, a surfactant, a binding agent, and a lubricant. Furthermore, it may be preferably formulated according to each disease or each component by using the method as disclosed in Remington's Pharmaceutical Science, Mack Publishing Company, Easton Pa. as a suitable method in the related art.

The present invention provides a use of a composition for preventing or treating inflammation, a use of a composition for preventing or treating inflammation by decreasing inflammatory cells (leukocytes, neutrophils, macrophages, and the like), a hematopoietic stem cell, a mononuclear cell, and an inflammatory cytokine (such as, TNF-alpha, IL2, IL4, IL6, and the like), in a blood, and a use of a composition for preventing or treating inflammation by increasing anti-inflammatory cytokines (such as IL10, and the like), anti-inflammatory regulatory T cells, and anti-inflammatory macrophages (M2), in blood, in which the composition includes Substance-P as an active ingredient.

Also, the present invention provides a use of a composition for preventing or treating inflammatory diseases or disorders selected from the group consisting of sepsis, arthritis, asthma, respiratory disease, respiratory syncitial virus (RSV) disease, inflammation induced by radiation, radiation injury, stomach ulcer, gastroenteritis, diabetic ulcer, bedsore, nerve spinal injury, dementia, cornea injury, skin wound, atopic dermatitis, cardiovascular disorders, autoimmune diseases, and rejection reaction of transplant.

Also, the present invention provides a use of a composition for preventing or treating inflammatory diseases or disorders selected from the group consisting of sepsis, arthritis, asthma, respiratory disease, respiratory syncitial virus (RSV) infection, gastritis, enteritis, gastroenteritis, and atopic dermatitis.

In addition, the present invention provides a use of a composition for preventing or treating inflammation, which is mediated by at least one selected from the group consisting of respiratory disease, radiation injury, stomach ulcer, diabetic ulcer, bedsore, nerve spinal injury, dementia, cornea injury, skin wound, cardiovascular disorders, autoimmune diseases, and rejection reaction of transplant.

The present invention provides a method for preventing and treating inflammation, preferably inflammatory diseases or disorders selected from the group consisting of sepsis, arthritis, asthma, respiratory disease, respiratory syncitial virus (RSV) disease, inflammation induced by radiation, radiation injury, stomach ulcer, gastroenteritis, diabetic ulcer, bedsore, nerve spinal injury, dementia, cornea injury, skin wound, atopic dermatitis, cardiovascular disorders, autoimmune diseases, and rejection reaction of transplant, in which the method includes administrating a therapeutically effective amount of Substance-P to a mammal.

Also, the present invention provides a method for preventing or treating inflammation, in which the method includes administrating a therapeutically effective amount of Substance-P to a mammal.

Also, the present invention provides a method for preventing or treating inflammatory diseases or disorders selected from the group consisting of sepsis, arthritis, asthma, respiratory disease, respiratory syncitial virus (RSV) infection, gastritis, enteritis, gastroenteritis, and atopic dermatitis, in which the method includes administrating a therapeutically effective amount of Substance-P to a mammal.

In addition, the present invention provides a method for preventing or treating inflammation, or inflammatory diseases or disorders, which are mediated by at least one or mediates at least one selected from the group consisting of respiratory disease, radiation injury, stomach ulcer, diabetic ulcer, bedsore, nerve spinal injury, dementia, cornea injury, skin wound, cardiovascular disorders, autoimmune diseases, and rejection reaction of transplant, in which the method includes administrating a therapeutically effective amount of Substance-P to a mammal.

As used herein, the term "a therapeutically effective amount" refers to the amount of active ingredient or pharmaceutical composition that induces biological or medical reactions in an animal or a human that may be considered by researchers, vets, doctors, or other clinicians, and includes the amount for inducing alleviation of symptoms of disease or disorder to be treated. It is clear to a person who has a common knowledge in the related art that an effective administration amount and administration number for treating with an active ingredient of the present invention may be changed according to a required effect. Accordingly, an optimal dose to be administrated can be easily determined by a person who has a common knowledge in the related art, and can be controlled by various factors, such as a type of disease, severity of disease, the amounts of an active ingredient and other components included in a composition, a type of dosage form, and an age, a weight, a general health condition, a sex, and a diet of a patient, an administration time, an administration route, a secretion rate of composition, a treating period, a drug of simultaneous use, and the like. For a method for preventing or treating an inflammation, preferably inflammatory diseases or disorders selected from the group consisting of sepsis, arthritis, asthma, respiratory disease, respiratory syncitial virus (RSV) disease, inflammation induced by radiation, radiation injury, stomach ulcer, gastroenteritis, diabetic ulcer, bedsore, nerve spinal injury, dementia, cornea injury, a skin wound, an atopic dermatitis, cardiovascular disorders, and autoimmune diseases; a method for preventing or treating inflammatory diseases or disorders selected from the group consisting of sepsis, arthritis, asthma, respiratory disease, respiratory syncitial virus (RSV) infection, gastritis, enteritis, gastroenteritis, and atopic dermatitis; or a method for preventing or treating inflammatory diseases or disorders, which are mediated by at least one or mediates at least one selected from the group consisting of respiratory disease, radiation injury, stomach ulcer, diabetic ulcer, a bedsore, nerve spinal injury, dementia, cornea injury, skin wound, cardiovascular disorders, autoimmune diseases, and rejection reaction of transplant, according to the present invention, it is preferable that an amount of 0.001-0.5 mg/day, preferably 0.0001-0.005 mg/kg, of Substance-P is administered in case of an adult when administrating one time per a day.

The composition according to the present invention may be administrated via an oral, subglossal, rectal, dermal, subcutaneous, intra-muscular, intra-abdominal, intra-venous, intra-arterial, intrathecal, intra-medullar route, and the like, and preferably may be administrated to a vein.

Also, the present invention provides a method for preventing, decreasing, inhibiting inflammation in an object, including administrating a therapeutically effective amount of Substance-P to the object to need to be treated.

Also, the present invention provides a method for preventing, decreasing, or inhibiting inflammation in an object, including administrating a therapeutically effective amount of Substance-P to the object to need to be treated to decrease hematopoietic stem cells in blood.

Also, the present invention provides a method for preventing, decreasing, or inhibiting inflammation in an object, including administrating a therapeutically effective amount of Substance-P to an object to need to be treated to decrease mononuclear cells in blood.

Also, the present invention provides a method for preventing, decreasing, or inhibiting inflammation in an object, including administrating a therapeutically effective amount of Substance-P to the object to need to be treated to decrease at least one selected from the group consisting of inflammatory cells, preferably leukocytes, neutrophils, and macrophages in blood or to increase at least one selected from the group consisting of anti-inflammatory cells, preferably anti-inflammatory regulatory T cells or anti-inflammatory macrophages (M2), in blood.

Also, the present invention provides a method for preventing, decreasing, or inhibiting inflammation in an object, including administrating a therapeutically effective amount of Substance-P to the object to need to be treated to decrease inflammatory cytokines (such as, TNF-alpha, IL2, IL4, IL6) or to increase anti-inflammatory cytokines (such as, IL10), in blood.

Also, the present invention provides a method for preventing, decreasing, or inhibiting inflammation in an object, including administrating a therapeutically effective amount of Substance-P to the object having inflammatory diseases or disorders selected from the group consisting of sepsis, arthritis, asthma, respiratory disease, respiratory syncitial virus (RSV) disease, inflammation induced by radiation, radiation injury, stomach ulcer, gastroenteritis, diabetic ulcer, bedsore, nerve spinal injury, dementia, cornea injury, skin wound, atopic dermatitis, cardiovascular disorders, autoimmune disease, and rejection reaction of transplant, or the risks thereof.

Also, the present invention provides a method for preventing, decreasing, or inhibiting inflammation in an object, including administrating a therapeutically effective amount of Substance-P to an object, in which the inflammation is mediated by at least one or mediates at least one selected from the group consisting of respiratory disease, radiation injury, stomach ulcer, diabetic ulcer, bedsore, nerve spinal injury, dementia, cornea injury, skin wound, cardiovascular disorders, autoimmune diseases, and rejection reaction of transplant.

Advantageous Effects

The composition comprising Substance-P according to the present invention exhibits effects of decreasing inflammatory cells, hematopoietic stem cells, mononuclear cells, and inflammatory cytokines as well as effects of increasing anti-inflammatory cytokines, anti-inflammatory regulatory T cells, anti-inflammatory macrophages (M2) in blood for the purpose of preventing or treating inflammation.

MODE FOR INVENTION

Figure 1:
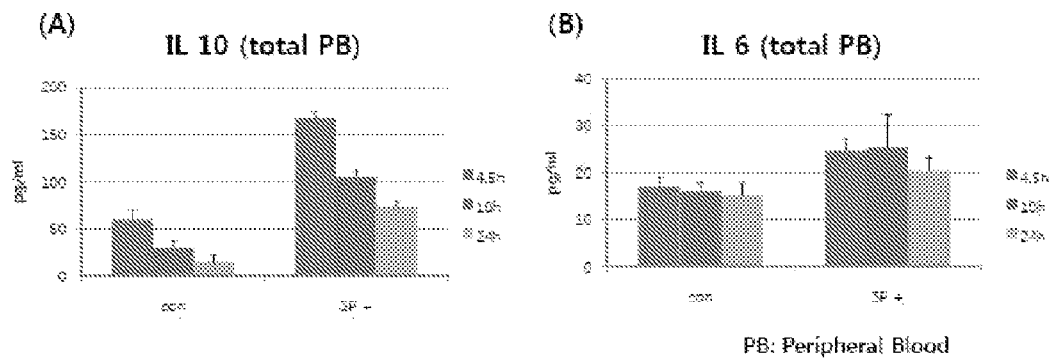
FIG. 1 is a graph showing expression levels of IL-6 and IL-10 when treating Substance-P to mononuclear cells isolated from peripheral blood.

Advantages and features of the present invention, and a method for achieving them will be clarified with reference to examples that will be described later. The present invention may, however, be embodied in different forms and should not be construed as limited to the examples set forth herein. Rather, these examples are provided so that the disclosure of the present invention will be thorough and complete, and will fully convey the scope of the present invention to those skilled in the art. The scope of the present invention should be defined by the appended claims.

EXAMPLE

Example 1

Confirmation of Anti-Inflammatory Effect of SP In Vitro

Example 1-(1)

Confirmation of Anti-Inflammatory Effect when Adding SP to Peripheral Blood

Peripheral blood was collected from C57bl/6 mice (8 weeks, sex; male, n=5, Average Weight; 20 g), diluted doubly with PBS, carefully placed on Ficoll in a tube, and then centrifuged at 2200 rpm for 20 minutes. By centrifuging, from the bottom, an erythrocyte layer, a ficoll layer, a mononuclear cell layer, and a plasma layer were obtained in order. The mononuclear cell layer and plasma layer were isolated, excluding the erythrocyte layer and ficoll layer, and then washed one time with PBS. Then, the number of cells was counted; the cells with a concentration of $1\times10^5/0.2$ ml were seeded onto T-cell activation media (lymphocyte activation media; RPMI, 10% FBS, 100 µM 2-mercaptoetanol, 20 µg/ml ConA); then the cells were cultured at an incubator of 37° C.; and then culture supernatant was taken at 4.5 hours, 10 hours, and 24 hours. For SP-treated group, 10 nmole/kg of SP dissolved in a physiological saline was treated to T-cell activation media. The blood cells were cultured at a culture media for 4.5 hours, 10 hours, and 24 hours, and then expression levels of IL-6 and IL-10 were confirmed in the culture supernatant by using ELISA (R&D System) method. Specific processes were as follows: culture supernatant samples stored in −70° C. and reagents, controls, and standard proteins stored in a cold storage were taken out at a room temperature. 50 µl of diluted solutions were put into each well; 50 µl of standard, control, and samples were added, respectively; well mixed by lightly tapping the plate; and then placed for 2 hours at a room temperature. After placing at a room temperature, the solution was removed out. Then, it was washed five times with a washing buffer; 100 µl of conjugate (IL-10 conjugate, IL-6 conjugate) was added to each well; and then placed for 2 hours at a room temperature. After placing at a room temperature, it was washed as the previous method; 100 µl of substrate solution was added; and then placed for 30 minutes at a room temperature while blocking out light. After 30 minutes, 100 µl of stop codon was treated to stop the reaction; the optical density was measured at 450 nm; the amounts of cytokines were converted based on a protein conversion formula by a standard sample; and then the results were shown in FIG. 1.

As shown in FIG. 1, it was found out that an anti-inflammatory cytokine, IL-10 was increased by treating SP, but there was no a significant difference about an inflammation-inducible cytokine, IL 6.

Example 1-(2)

Confirmation of Anti-Inflammatory Effect of CD4+ T Cell and CD11b+ Macrophage when Adding SP Peripheral blood was collected with the same method as Example 1-(1); and RBC and ficoll layers were removed out with Ficoll method and isolated by using MACS (Miltenyi Biotec, Germany) cell isolation method.

The isolation processes were as follows: CD4-FITC (130-091-608, Miltenyi Biotec, Germany) antibody was treated for 10 minutes and anti-FITC Microbeads (120-000-293, Miltenyi Biotec, Germany) was treated for 15 minutes; and then loaded on MACS column to isolate CD4+ T cell. Then, CD4+ T cell with a concentration of $1 \times 10^4/0.2$ ml were cultured in T-cell activation media at 37° C. incubator as the Example 1-(1), and then the culture supernatant was taken at 4.5 hours, 10 hours, and 24 hours. Also, CD11b-FITC (130-081-201, Miltenyi Biotec, Germany) antibody were treated for 10 minutes and anti-FITC Microbeads was treated for 15 minutes; and then loaded on MACS column to isolate CD11b+ macrophage. Then, CD11b+ macrophage with a concentration of $2 \times 10^3/0.2$ ml was cultured in macrophage activation media (a-MEM, 10% FBS, 100 μM 2-mercaptoetanol, 20 μg/ml ConA) at 37° C. incubator, and then the culture supernatant was taken at 4.5 hours, 10 hours, and 24 hours. The treatment of SP and the confirmation of expressions of IL-10 and IL-6 were performed with the same methods as Example 1-(1).

Figure 2:
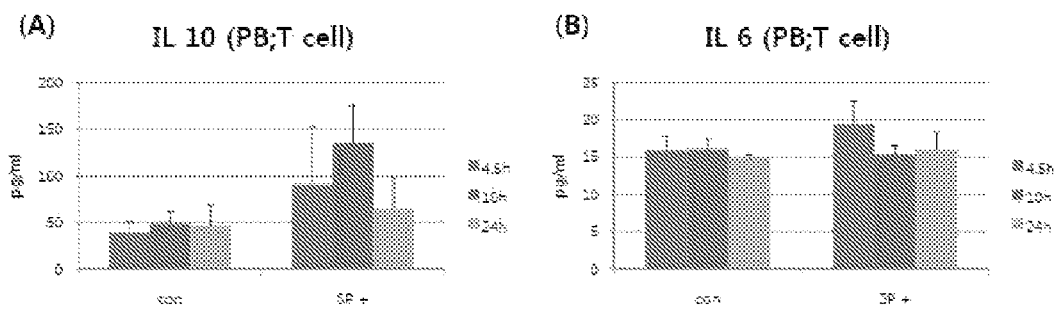
FIG. 2 is a graph showing expression levels of IL-6 and IL-10 when treating Substance-P to CD4+ T cell isolated from peripheral blood.
Figure 3:
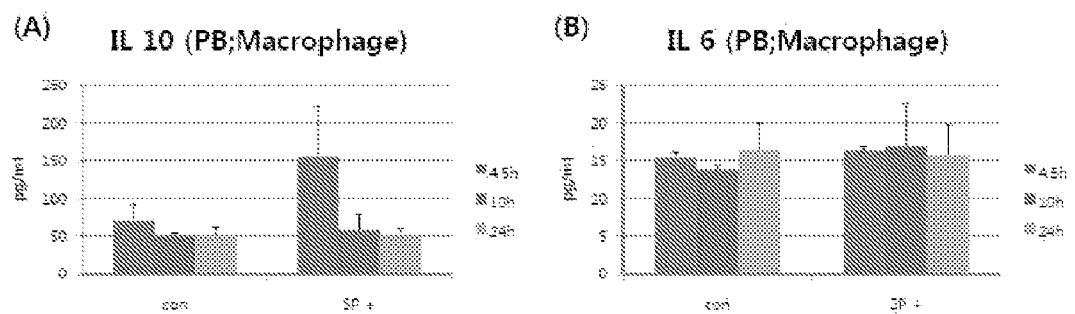
FIG. 3 is a graph showing expression levels of IL-6 and IL-10 when treating Substance-P to CD11b+ macrophage isolated from peripheral blood.

The results were shown in FIGS. 2 and 3.

As shown in FIGS. 2 and 3, it was found out that by treating SP, the expression of an anti-inflammatory cytokine, IL-10 was increased in CD4+ T cell and CD11b+ macrophage, but there was no difference in an expression level of a pro-inflammatory cytokine, IL-6.

Example 2

Confirmation of Anti-Inflammatory Effect by Administrating SP in Corneal Epithelial Burn Model Ketalar (50 mg/ml, Yuhan Corporation) and Rompun (23.32 mg (Xylazine hydrochloride)/ml, Bayer Korea Corporation) were mixed in a rate of 2:1, and then total 900 μl (Ketalar 600 μl: Rompun 300 μl) was injected into muscles of rabbits (New Zealand white rabbit, Male, 2.5 kg, n=4). After the intramuscular injection, 300 μl (Ketalar 200 μl: Rompun 100 μl) of the same anesthetic drug was injected in the rabbit's ear vein.

A 6 mm paper disc fully wetted by 1N NaOH was contacted to a limbus part of rabbit's cornea for 10 seconds. After alkali burning, corneal epithelium was removed in a size of the paper disc. The rabbit's eyes were quickly washed with a physiological saline immediately after alkali burning. At the same time, 5 nmole/kg of SP dissolved in a physiological saline was intravenously injected, and then after 24 hours, was injected once more (immediately after burning and at 24 hours after burning). For the control, PBS with the same volume was injected (injection Volume: 1 ml).

Peripheral blood was collected from ear veins in 10 ml at one, three, five and seven days after alkali burning. 2 ml of the isolated blood was used for measuring leukocytes levels and the remaining 8 ml was used for isolating cells.

Example 2-1

Confirmation of Effect of Early-Decreasing the Number of Mononuclear Cells in Blood by Administrating SP The blood obtained from the above step was diluted twice with PBS, and then carefully put on Ficoll in a tube. Since then, it was centrifuged at 2200 rpm for 25 minutes. By centrifuging, from the bottom, a leukocyte layer, ficoll layer, a mononuclear cell layer and a plasma layer were obtained, and then the plasma layer was removed out to isolate only mononuclear cells and put in a new tube. Then, after adding 30 ml of PBS and centrifuging (washing step), the number of cells was counted to confirm the number of cells per 1 ml and then the results were shown in FIG. 4.

Figure 4:
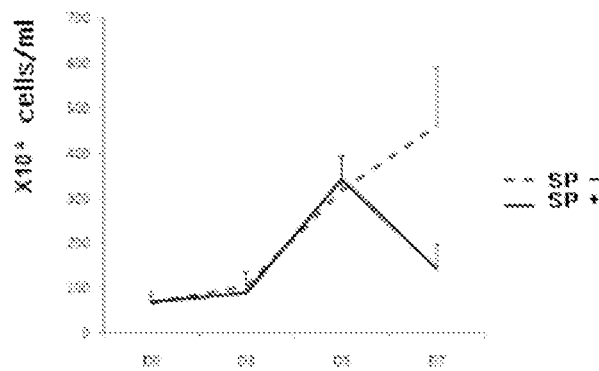
FIG. 4 is a graph showing an effect of early-decreasing mononuclear cells in blood by administrating Substance-P, wherein the number of mononuclear cells was increased by inflammation.

The number of cells was the number of blood cells including inflammatory cells and was proportional to an overall inflammation level. As shown in FIG. 4, it could be found that the total number of cells was maintained similarly at early stage after burning, but for the group without injecting Substance-P, it was continuously increased while for the group with injecting Substance-P, it was decreased at seven days. Accordingly, it could be known that Substance-P contributed to inflammation treatment through a decrease of the number of inflammatory cells.

Example 2-2

Figure 5:
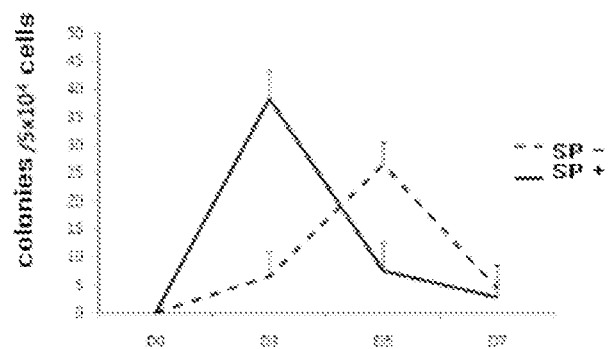
FIG. 5 is a graph showing an effect of early-terminating a movement of hematopoietic stem cells into blood by administrating Substance-P, wherein the movement of HSCs was caused by inflammation.

Confirmation of Effect of Early-Decreasing the Number of Hematopoietic Stem Cells in Blood by Administrating SP $1 \times 10^4$ cells among the whole cells was used for HSC-CFU assay. At this time, semi-solid HSC-CFU media (Miltenyi; Hematopoietic stem cell-colony forming unit) was used as a media, and 2 ml of the media was put in 35 mm dish. The cells were cultured in the media for 2 weeks (5% $CO_2$, 37° C.), the number of colonies was counted by using a microscope (Leica) and then the results were shown in FIG. 5.

As shown in the results of comparing the numbers of HSC between two groups, it was confirmed that while it was increased at early stage and then decreased immediately three days after injection for the group with injecting Substance-P, it was gradually increased, has a peak at five days, and then was gradually started to decrease for the group without injecting Substance-P. Accordingly, it could be confirmed that through administrating Substance-P, the time of moving hematopoietic stem cells into blood stream was terminated in early stages. The result refers that Substance-P shortens a period of inflammation.

Example 2-3

Confirmation of Effect of Early-Decreasing the Number of Leukocytes in Blood by Administrating SP 2 ml of the whole 10 ml was used for counting blood cells and the number of leukocytes was analyzed in Neodin (Company for analysis of blood cells). Concretely, 2 ml of blood was added to a vial including EDTA; it was well mixed; then the whole leukocyte level was analyzed in an automatic analyzer (SYSMEX XE-2100 automatic analyzer from SYSMEX Corporation [Japan]); and then the results were shown in FIG. 6.

Figure 6:
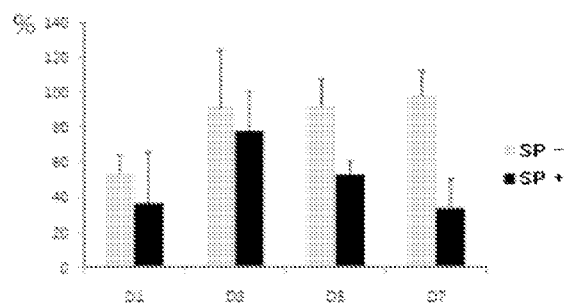
FIG. 6 is a graph showing an effect of decreasing the number of leukocytes in blood by administrating Substance-P, wherein the number of leukocytes was increased by inflammation.

FIG. 6 shows an increase % based on Day 0-level. As shown in FIG. 6, it was found that the numbers of leukocytes for each group were similar up to three days after burning, but it was sharply decreased for the group with injecting Substance-P while it was continuously increased for the group without injecting Substance-P. Accordingly, an effect of decreasing the number of leukocytes in blood by administrating Substance-P was confirmed. The result means that Substance-P rapidly terminates inflammation.

Example 3

Confirmation of Anti-Inflammatory Effect by Administrating SP in Radiation-Irradiating Model It is already known that for a radiation-irradiated gastrointestinal system, severe inflammation is caused by a cell necrosis so that inflammation of gastrointestinal system including gastroenteritis is caused. Accordingly, it is pointed out as a representative damage of radiation treatment.

5 nmole/kg of SP dissolved in a physiological saline was injected to a tail vein of C57b1/6 mice (8 weeks, sex; male, n=4, Average weight; 20 g) one day before irradiation and immediately after irradiation. The irradiation was performed at 8 Gy radiation in a Gamma lay radiation irradiator ($^{137}$Cs, Atomic Energy of Canada, Mississauga, Canada). The mice were sacrificed at 4.5 hours and one day after irradiation, and then the blood was collected. The part of the blood was used for analyzing CBC (Complete Blood Count) and the remaining blood was used to isolate serum and then analyze cytokines

Example 3-1

Figure 7:
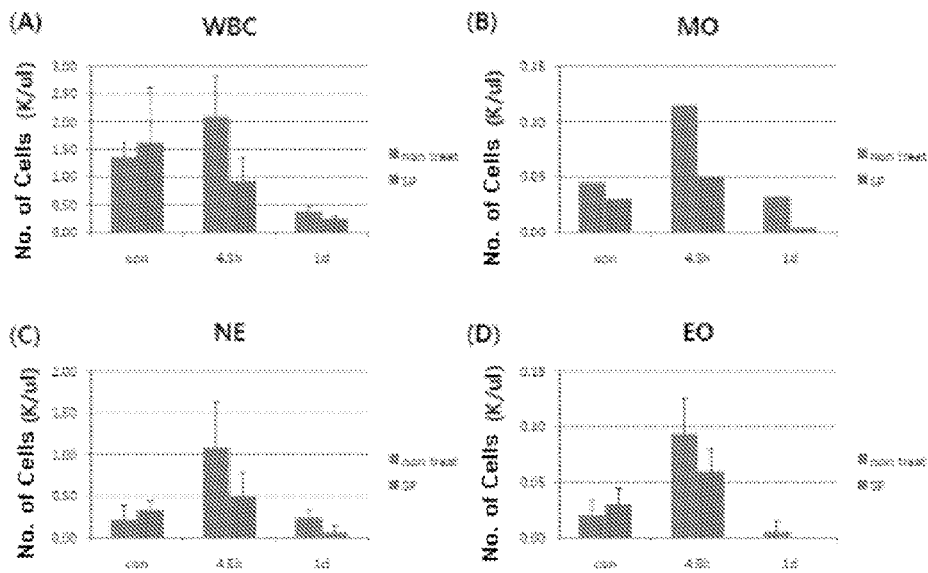
FIG. 7 is a graph showing an effect of decreasing the number of inflammatory cells by administrating Substance-P, wherein the number of inflammatory cells was increased by irradiation.

Confirmation of Inhibiting Effect of SP on the Increase of Inflammatory Cell in Blood Caused After Irradiation 200 μl of mouse's blood was taken at 4.5 hours and one day after 8 Gy radiation; it was added to a vial including a small amount of EDTA and then analyzed for CBC. As a result, it was confirmed that an increase of inflammatory cells in blood was observed at 4.5 hours after irradiation and the number of inflammatory cells was significantly decreased for the group with injecting SP. As shown in FIG. 7, A) leukocyte (White Blood Cell), B) mononuclear cell, and C) neutrophilic leukocyte were decreased at least two times as compared with the group without injecting SP, and D) eosinocyte was also decreased by 30-40%. It was confirmed that SP has an effect of inhibiting an increase of inflammatory cells caused by irradiation.

Example 3-2

Figure 8:
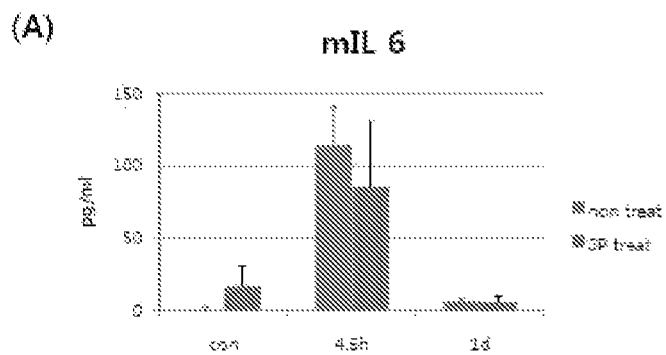
FIG. 8 is a graph showing an effect of decreasing inflammatory cytokines by administrating Substance-P, wherein the amounts of inflammatory cytokines were increased by irradiation.
Figure 8:
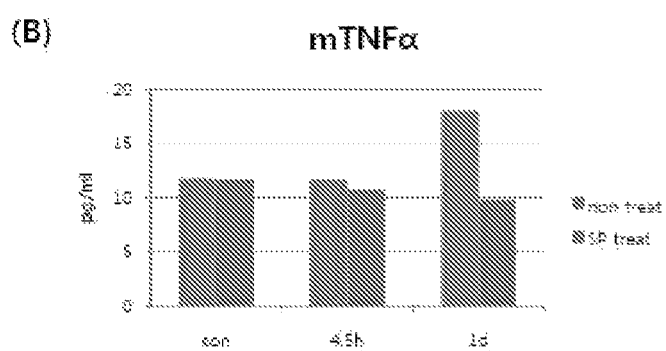

Confirmation of Inhibiting Effect of SP on the Increase of Inflammatory Cytokines in Blood After Irradiating Radiation IL-6 and TNFα that are well known as inflammatory cytokines were analyzed. Specific procedures were as follows: Serum samples stored in 70° C. and reagents, controls, and standard proteins stored in a cold storage were taken out at a room temperature. 50 μl of diluted solution was put into each well; 50 μl of standard, control, and samples were added; well mixed by lightly tapping the plate; and then placed for 2 hours at a room temperature. After placing at a room temperature, the solution was removed out; it was washed five times by using the supplied washing buffer; 100 μl of conjugate (IL-6 conjugate, TNF α conjugate) was added to each well; and then placed for 2 hours at a room temperature. After placing at a room temperature, it was washed by using the same method as the previous one; 100 μl of substrate solution was added; and then placed for 30 minutes at a room temperature while blocking out light. After 30 minutes, 100 μl of stop codon was treated to stop the reaction; the optical density was measured at 450 nm; the amounts of cytokines were converted based on a protein conversion formula by a standard sample; and then the result was shown in FIG. 8. As shown in FIG. 8A, it was confirmed that an inflammatory cytokine, IL-6 was increased at 4.5 hours after irradiation, but for the group with injecting SP, an increase of IL-6 was inhibited by about 30% as compared with the group without injecting SP. Also, it was confirmed that TNF α was inhibited at one day after irradiation for the group with injecting SP.

Example 3-3

Figure 9:
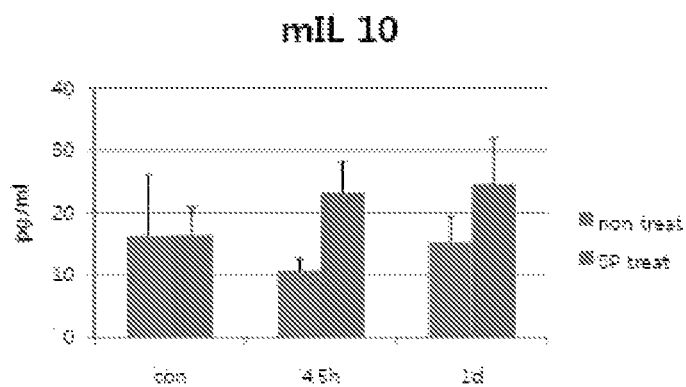
FIG. 9 is a graph showing an effect of increasing anti-inflammatory cytokines by administrating Substance-P, wherein the amounts of anti-inflammatory cytokines were decreased by irradiation.

Confirmation of Effect of Increasing Anti-Inflammatory Cytokines in Blood by Administrating SP After Irradiating Radiation IL-10 that is well known as an anti-inflammatory cytokine was analyzed with ELISA (R&D System) by using the same method as Example 2-2. As shown in FIG. 9, it was confirmed that IL-10 was decreased at 4.5 hours after irradiation, but the amount of IL-10 was increased by at least two times for the group with injecting SP and was also increased at one day for the group with injecting SP.

Example 3-4

Confirmation of Increases of Regulatory T Cells and Anti-Inflammatory Macrophages (M2) of Mesentric Lymph Node (MLN) by Administrating SP After Irradiating Radiation The mice were sacrificed at 4.5 hours after irradiation using the same method as Example 3; mesentric lymph nodes were taken for isolating mononuclear cells; then isolated mononuclear cells were fixed at 3.7% formalin for 1 hour; and then anti-inflammatory-related T cells and macrophages were analyzed through FACS (BD FACSCalibur™: 343098, BD Biosciences, Canada) analysis.

Specifically, the mice were sacrificed at 4.5 hours after 8 Gy radiation; the abdomens were cut to open; mesentric lymph nodes and small intestines were taken and then were cut fine; then chopped by using operating scissors; then were treated with collagenase type I (Worthington, USA) and DNase I (Sigma, USA) at 37° C. for 20 minutes; washed, respectively; mononuclear cells were isolated; and then fixed in 3.7% formalin for 1 hour. The mesentric lymph nodes mononuclear cells fixed in formalin were double-stained with CD4 (130-091-608, Miltenyi Biotec, Germany) and FoxP3 (130-093-013, Miltenyi Biotec, Germany) antibody, and then regulatory T cells were analyzed through FACS analysis. In addition, an anti-inflammatory macrophage M2 analysis was performed through FACS analysis after double staining with CD11b (130-081-201, Miltenyi Biotec, Germany) and CD206 (ab64693, abcam, UK) antibody. Since T cells or macrophages in the small intestine mononuclear cells fixed in a formalin accounted for less than 1% of the whole cells, FACS analysis was performed after isolating CD3 (130-092-962, Miltenyi Biotec, Germany)+ cell and CD11b+ cell with MACS isolating method as disclosed in the previous Example 1-(2), respectively. Regulatory T cells were analyzed by double-staining the cells isolated by CD3 with CD4 and FoxP3 antibody and anti-inflammatory macrophage M2 analysis was performed by double-staining the cells isolated by CD11b with CD11b and CD206 antibody. The results were shown in FIGS. 10 and 11.

Figure 10:
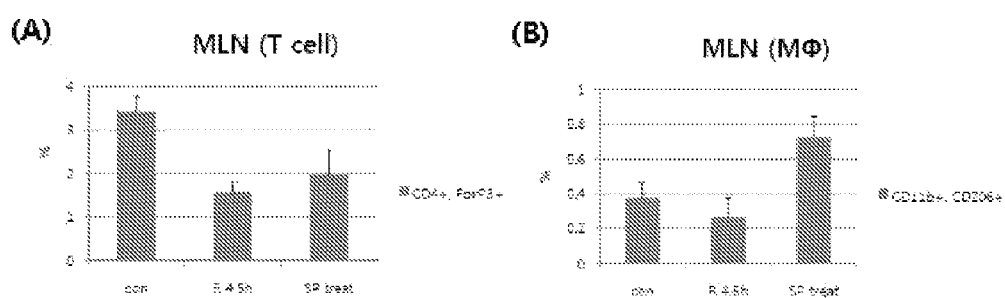
FIG. 10 is a graph showing effects of increasing anti-inflammatory macrophages (M2) and anti-inflammatory regulatory T cells of mesenteric lymph nodes (MLN) by administrating Substance-P.
Figure 11:
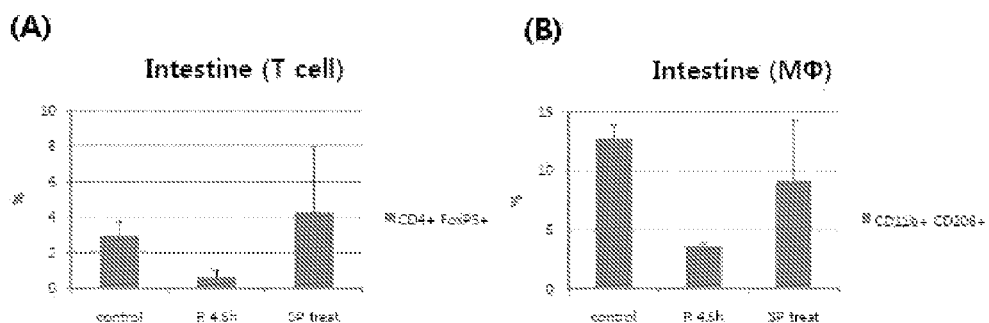
FIG. 11 is a graph showing effects of increasing anti-inflammatory macrophages (M2) and anti-inflammatory regulatory T cells of small intestine by administrating Substance-P.

As shown in FIGS. 10 and 11, it was found that anti-inflammatory macrophage M2 (CD11b+, CD206+) and regulatory T cells (CD4+, FoxP3+) of the mesentric lymph nodes and small intestines were increased in the group with injecting SP.

Example 4

Confirmation of Effect of Preventing or Treating Autoimmune Diseases by Anti-Inflammatory Function of SP Autoimmune diseases, such as diabetes, as well as various inflammatory diseases, are also known to be induced by excessive immune responses. The diabetes induced by Streptozotocin (hereinafter, called as to STZ) that is Type I diabetes is known as an autoimmune disease of pancreas or pancreas-related lymphatic tissue. It was confirmed that when diabetes was induced with Streptozotocin, progress to Type I diabetes was inhibited by treating SP, and also diabetes lesion became weak when treating SP after inducing diabetes.

Specifically, 5 nmole/kg of SP dissolved in a physiological saline was injected to a tail vein of ICR mouse (8 weeks, sex; male, n=10, Average Weight: 30 g), and then STZ (Sigma, USA) was intraabdominally injected. Streptozotocin was daily injected intraabdominally for two days, and SP was intravenously injected at the same concentration for five days. Only streptozotocin was injected for the control; after one week, blood glucose level was checked to confirm induction of diabetes; then SP was intravenously injected for five days from seven days after STZ injection.

1) STZ-injected group (n = 10): group with intra-abdominally injecting STZ and at the same time, intravenously injecting PBS for five days.
2) STZ/SP-injected group (n = 10): group with intra-abdominally injecting STZ and at the same time, intravenously injecting SP for five days.
3) STZ/after SP-injected group (n = 10): group with intra-abdominally injecting STZ and after seven days, intravenously injecting SP for five days after confirming induction of diabetes.

Figure 13:
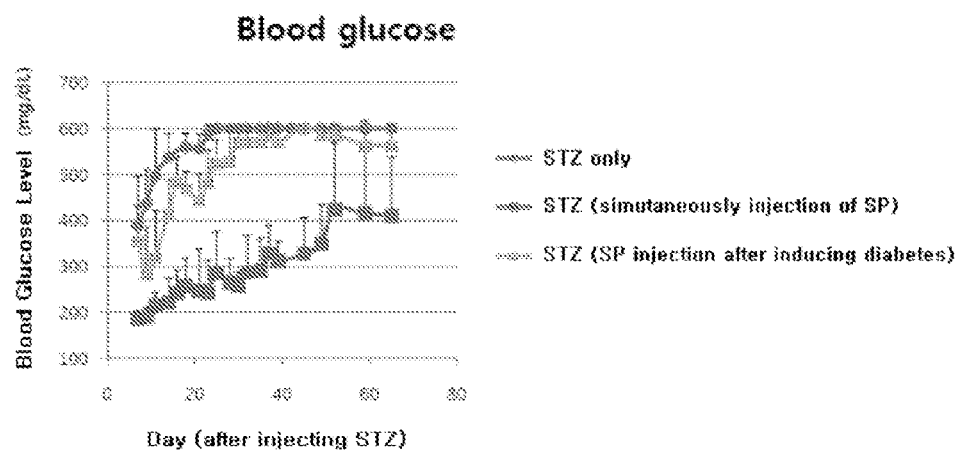
FIG. 13 is a graph showing an effect of maintaining blood glucose level by concurrently administrating Substance-P when autoimmune diabetes is induced by administrating streptozotocin.
Figure 14:
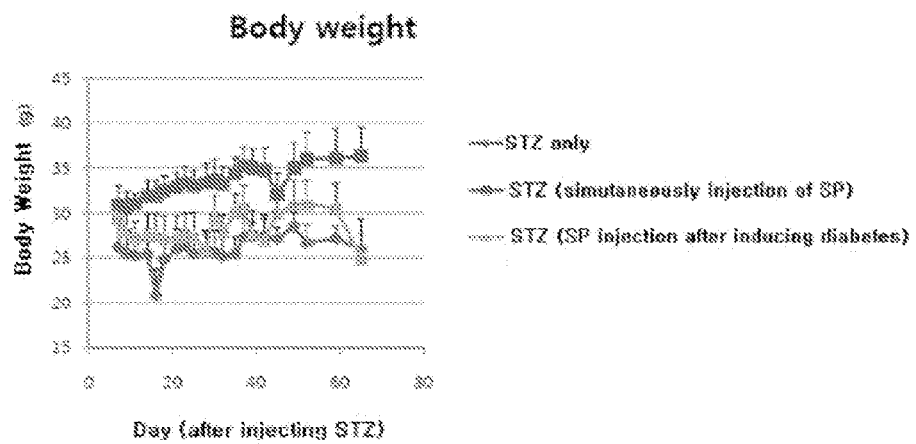
FIG. 14 is a graph showing an effect of maintaining weight by concurrently administrating Substance-P when autoimmune diabetes is induced by administrating streptozotocin.

Blood glucose level and weight were investigated. One drop of blood was taken from a tail vein of mouse by one time per 2-3 days, and a blood glucose level was measured by using a glucometer (Roche, Switzerland) and a weight was measured. The results were shown in FIGS. 13 and 14. While the blood glucose levels and weight were maintained in normal state for the group with injecting SP and STZ at the same time (No. 2 in the above box), all of 10 mice exhibited at least 600 that is the highest blood glucose level after 20 days of injection for the group with only injecting STZ (No. 1 in the above box). It was confirmed the effect that the blood glucose level was decreased in the short run when injecting SP for the group with injecting SP after inducing a diabetes (Top Box No. 3).

Figure 12:
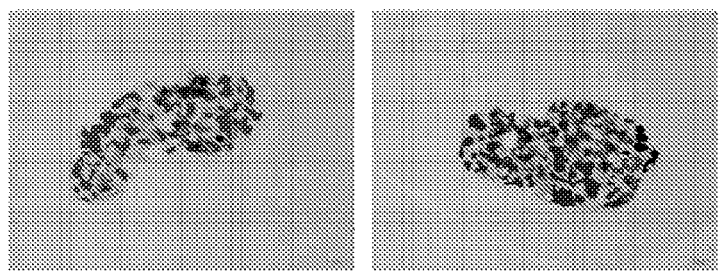
FIG. 12 is a diagram showing effects of inhibiting an autoimmune injury of pancreas beta cells by concurrently administrating Substance-P when autoimmune diabetes is induced by administrating streptozotocin.
Figure 12:
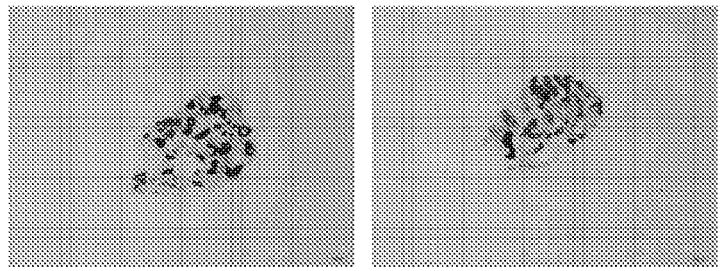
Figure 12:
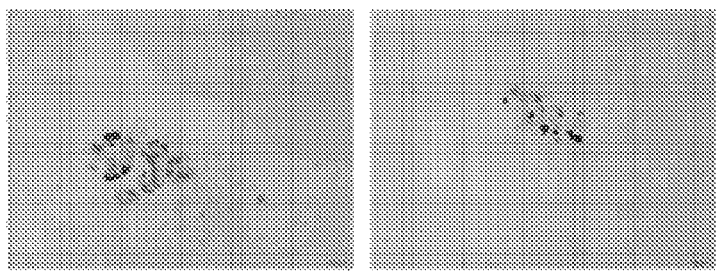

The mice were sacrificed at 11 weeks, the pancreases were isolated, and then Insulin IHC staining (4590, Cell Signaling, USA) was performed. The results were shown in FIG. 12. As shown in FIG. 12, while insulin secretion of the group with injecting SP was high, an insulin secretion of the group with only injecting STZ was significantly low. That means that death of beta cells secreting insulin was inhibited by SP, and prevention and inhibition effects of autoimmune diseases in a pancreas were confirmed. That is, it was confirmed that SP inhibits a progress of Type I diabetes, and diabetes lesion becomes weak when treating SP after inducing diabetes. These anti-inflammatory effects of Substance P seem to result in the prevention or treatment of autoimmune diseases, such as diabetes, as well as an inflammatory diseases.

The invention claimed is:

1. A method for decreasing or inhibiting inflammation in an animal or human, comprising administering a therapeutically effective amount of Substance-P to the animal or human to be treated, wherein the therapeutically effective amount of Substance-P is 0.001-0.5 mg/day or 0.0001-0.005 mg/kg.

2. The method of claim 1, wherein the administration of Substance-P decreases hematopoietic stem cells in blood, thereby decreasing or inhibiting inflammation in the animal or human.

3. The method of claim 1, wherein the administration of Substance-P decreases mononuclear cells in blood, thereby decreasing or inhibiting inflammation in the animal or human.

4. The method of claim 1, wherein the administration of Substance-P decreases inflammatory cells in blood, thereby decreasing or inhibiting inflammation in the animal or human.

5. The method of claim 4, wherein the inflammatory cells are at least one selected from leukocytes, neutrophils, or macrophages.

6. The method of claim 1, wherein the administration of Substance-P decreases inflammatory cytokines in blood, thereby decreasing or inhibiting inflammation in the animal or human.

7. The method of claim 1, wherein the administration of Substance-P increases anti-inflammatory cytokines in blood, thereby decreasing or inhibiting inflammation in the animal or human.

8. The method of claim 1, wherein the administration of Substance-P increases at least one selected from regulatory T lymphocytes or anti-inflammatory macrophages, thereby decreasing or inhibiting inflammation in the animal or human.

9. The method of claim 1, wherein the human or animal to be treated has inflammatory diseases or disorders, or the risk thereof, selected from arthritis, inflammation induced by radiation, radiation injury, diabetic ulcer, cornea injury, skin wound, or myocardial infarction.

10. The method of claim 1, wherein the inflammation is mediated by at least one or mediates at least one selected from radiation injury, diabetic ulcer, cornea injury, skin wound, or myocardial infarction.

* * * * *